(12) United States Patent
Dan et al.

(10) Patent No.: US 8,481,319 B2
(45) Date of Patent: Jul. 9, 2013

(54) COMPOSITIONS AND METHODS FOR MODULATING OXIDATIVE BURST IN PLANT TRANSFORMATION

(75) Inventors: Yinghui Dan, Danville, VA (US); Manuel B. Sainz, Brisbane (AU); Heng Zhong, Durham, NC (US); Liang Shi, Durham, NC (US)

(73) Assignee: Syngenta Partcipations AG, Basel (CH)

( * ) Notice: Subject to any disclaimer, the term of this patent is extended or adjusted under 35 U.S.C. 154(b) by 0 days.

(21) Appl. No.: 12/800,895

(22) Filed: May 25, 2010

(65) Prior Publication Data

US 2010/0325754 A1   Dec. 23, 2010

Related U.S. Application Data

(60) Provisional application No. 61/269,266, filed on Jun. 23, 2009.

(51) Int. Cl.
*C12N 5/00* (2006.01)
*C12N 5/02* (2006.01)

(52) U.S. Cl.
USPC ........................................... 435/431

(58) Field of Classification Search
USPC .......... 800/294, 301, 278, 279, 298; 548/507; 435/431
See application file for complete search history.

(56) References Cited

U.S. PATENT DOCUMENTS 6,974,895 B1 * 12/2005 Paiva et al. .................... 800/301
2004/0133938 A1   7/2004 Dan et al.

OTHER PUBLICATIONS

Perl et al., Nature Biotechnol., 1996, 14, 5, pp. 624-628.
Enriquez-Obregon et al., Biotechnol. Aplication, 1997, 14, pp. 169-174.
Enriquez-Obregon et al., Planta, 1998, 206, pp. 20-27.
Enriquez-Obregon et al., Plant Cell, Tissue and Organ Culture, 1999, 59, 3, pp. 159-168.
Frisch et al., Plant Molecular Biology, 1995, 27, pp. 405-409 411.
De La Riva et al., Electronic J. Biotechnol., 1998, 1, 3, pp. 118-133.
Das et al., Plant Cell Rep, 2002, 20, 11, pp. 999-1005.
Olhoft et al., Plant Cell Rep, 2001, 20, pp. 731-737.
Olhoft et al., Plant Cell Rep, 2001, 20, pp. 706-711.
Olhoft et al., Planta, 2003, 216, pp. 723-735.
Dan, In Vitro Cell Dev Biol Plant, 2006, 42, 18-A (Abstract).
Dan et al., Plant Cell Rep, 2006, 25, pp. 432-441.
Dan, In Vitro Cell Dev Biol Plant, 2008, 44, 3, pp. 149-161.
Dekeyser, Plant Physiol, 1989, 20, pp. 217-223.
Della-Cioppa et al., Bio/Technology, 1987, 5, pp. 579-584.
Southern, J Mol Biol, 1975, 98, pp. 503-517.
Gamborg et al., Exp Cell Res, 1968, 50, pp. 151-158.
Murashige et al., Physiol Plant, 1962, 15, pp. 473-497.
Chih-Ching et al., Scientia Sinica, 1975, 18, pp. 659-668.
Linsmaier et al., Physio Plant, 1965, 18, pp. 100-127.
Duncan et al., Planta, 1985, 165, pp. 322-332.
McCown et al., HortScience, 1981, 16, 3, p. 453.
Nitsch et al., Science, 1969, 163, pp. 85-87.
Schenk et al., Can J Bot, 1972, 50, pp. 199-204.

* cited by examiner

*Primary Examiner* — Kent L Bell
(74) *Attorney, Agent, or Firm* — Bruce Vrana

(57) ABSTRACT

A method for introducing a nucleic acid sequence into the genome of a plant cell and regenerating a transformed plant therefrom, including culturing the plant cell on at least one plant transformation media, the at least one plant transformation media comprising an effective amount of a compound or compounds which may modulate oxidative burst, such as melatonin, 6-hydroxy melatonin (a melatonin analog), N-t-butyl hydroxylamine (NtBH), thiamazole, 1,3 dimethylthiourea, Resveratrol, epicatechin, NADPH, or NADH.

13 Claims, No Drawings

COMPOSITIONS AND METHODS FOR MODULATING OXIDATIVE BURST IN PLANT TRANSFORMATION

FIELD OF THE INVENTION

The present invention relates to plant tissue culture media and methods designed to more efficiently obtain transgenic plant cells and regenerated plants therefrom.

BACKGROUND

The invention relates to the production of transgenic plants involving plant cells or tissue being transformed with a gene of interest and then regenerated into whole plants. Representative current methods for transforming plants by introducing a gene of interest can require that the cells or tissue be maintained in plant culture media for several weeks to effect selection or to support sufficient tissue growth. Many commercially important plants, plant cells, or plant tissues are difficult to maintain in tissue culture, and this poses a limitation on the number of transgenic plants that can successfully be regenerated from tissue culture. One reason posed to explain the difficulty of culturing plant tissue in vitro is that the plant tissue/cells are stressed when forced to grow in tissue culture media. Potential reasons for this could include production of free radicals or reactive oxygen species during an oxidative burst, which damages cells, or activation or alteration of metabolic pathways.

Thus, there is a continuing need to provide plant transformation media that enhance effective selection and growth of transformed tissue/cells to survive in the media during the transformation/regeneration process. The present invention includes a media and method that increases the overall efficiency of the transformation process.

SUMMARY

A composition and method for genetically transforming a plant cell, tissue or other suitable explant and regenerating a transformed plant therefrom is provided. In accordance with the presently disclosed subject matter, the method provides for introducing a nucleic acid into the genome of a plant cell wherein an effective amount of a compound or compounds which modulate oxidative burst, such as melatonin, 6-hydroxy melatonin (a melatonin analog), N-t-butyl hydroxylamine (NtBH), thiamazole, 1,3 dimethylthiourea, resveratrol, epicatechin, NADPH, or NADH, is included in the transformation media. Compounds or modulators which modulate oxidative burst would include antioxidants and also non-antioxidants. In the practice of the method, the plant cell, tissue or explant is placed in contact with a transformation media comprising an amount of melatonin or a melatonin analog such as 6-hydroxy melatonin sufficient to enhance the efficiency of transformation and/or regeneration, and/or the survivability of the plant cell, tissue or explant compared to such transformation efficiency of tissue or explant where melatonin or an analog thereof is not included in the transformation media.

The present invention further provides plant transformation media comprising an effective amount of a compound or compounds which modulate oxidative burst, such as melatonin, 6-hydroxy melatonin (a melatonin analog), N-t-butyl hydroxylamine (NtBH), thiamazole, 1,3 dimethylthiourea, resveratrol, epicatechin, NADPH, or NADH. The media can be liquid, solid or semi-solid, and a compound or compounds which modulate oxidative burst can be included in any of the particular media used during the "transformation process", e.g., the inoculation, co-cultivation, delay, selection, shoot induction, elongation, regeneration or rooting media. The compounds of the invention can also be used in one or more of such particular media used during the "transformation process."

Also provided is a method of the invention for improving the efficiency of transformation and/or regeneration of a plant cell, tissue or explant in the presence of a compound or compounds which modulate oxidative burst, wherein the compound or compounds which modulate oxidative burst are included in the plant transformation media in which the plant cells, tissue or explant are cultured during the transformation process.

Further provided is a method of the invention for improving the efficiency of transformation and/or regeneration of a plant cell, tissue or explant in the presence of a compound or compounds, wherein the compound or compounds are included in the plant transformation media in which the plant cells, tissue or explant are cultured during the transformation process.

The present invention also provides a method for transforming dicotyledonous and monocotyledonous plant tissue and regenerating fertile transgenic plants therefrom comprising the inclusion of an effective amount of a compound or compounds in at least one of the plant transformation media during the transformation process.

The present invention also provides a method for transforming dicotyledonous and monocotyledonous plant tissue and regenerating fertile transgenic plants therefrom comprising the inclusion of an effective amount of a compound or compounds which modulate oxidative burst in at least one of the plant transformation media during the transformation process.

The present invention also provides using an effective amount of compound or compounds which modulate oxidative burst in one or more plant transformation media during the transformation process, sufficient to enhance the efficiency of transformation and/or regeneration, and/or the survivability of the plant cell, tissue or explant, compared to such transformation efficiency of tissue or explant where the compound or compounds which modulate oxidative burst are not included in the transformation media.

The present invention also provides using an effective amount of compound or compounds which modulate oxidative burst in one or more plant transformation media during the transformation process, sufficient to enhance the efficiency of transformation and/or regeneration, and/or the survivability of the plant cell, tissue or explant, compared to such transformation efficiency of tissue or explant where the compound or compounds which modulate oxidative burst are not included in the transformation media, wherein the compound or compounds which modulate oxidative burst are selected from any one or more of the group consisting of melatonin, 6-hydroxy melatonin (a melatonin analog), N-t-butyl hydroxylamine (NtBH), thiamazole, 1,3 dimethylthiourea, resveratrol, epicatechin, NADPH, or NADH.

An object of the present invention having been stated hereinabove, and which is achieved in whole or in part by the presently disclosed subject matter, other objects will become evident as the description proceeds when taken in connection with the accompanying drawings as best described herein below.

Definitions

"Transformation media" or "plant transformation media" as used herein, refers to the plant tissue culture media, whether liquid, solid or semi-solid, used during the process of the transformation of plant cells, tissues, parts or other plant tissue explants and subsequent regeneration of whole, transgenic plants therefrom. Depending upon the plant species being transformed and the transformation process being used, the transformation media can include, but is not limited to, the isolation media, induction media, delay media, selection media and/or regeneration media.

"Efficiency of transformation or regeneration" or "transformation efficiency," as used herein, refers to the percentage of transgenic events produced per explant or the percentage of transgenic plants produced per explant. The efficiency of transformation can also be described in the number of "escapes" resulting from the transformation process.

"Survivability" of a plant cell, tissue, part or other explant during the transformation and regeneration process, as used herein, refers to the ability of the cell, tissue, part or other explant to flourish in the transformation media with little or no browning or other disadvantageous characteristics that limit its ability to continue to divide and grow in the media.

An "event," as used herein, refers to a particular genomic insertion of the desired gene into a specific plant.

An "escape," as used herein, refers to a plant, a plant cell, or plant tissue that survives the selection process without having the gene encoding for resistance to the selectable marker stably transformed into the genome of said plant.

A "plant stress condition," as used herein, refers to less than optimal conditions necessary for maintaining healthy growth or maintenance of plant cells or tissue in plant transformation media, such as by repeated media transfers, limiting nutrients (including water and light), or less than optimal quality of plant tissue or cells such as by wounding or excessive handling. This list is not intended to be exclusive of other stress conditions known to those of ordinary skill in the art.

"Explant", as used herein, refers to isolated cells of a plant or plant tissue. An explant can be a portion of the shoot, leaves, or cells from other plant tissues.

A "transgenic event", as used herein, refers to a plant cell which comprises a nucleotide sequence inserted into its genome.

The terms "heterologous" and "exogenous", when used herein to refer to a nucleotide sequence that originates from a source foreign to the particular host cell or, if from the same source, is modified from its original form. The terms also include non-naturally occurring multiple copies of a naturally occurring DNA sequence. Thus, the terms refer to a DNA segment that is foreign to the host cell, or naturally occurring in the host cell but in a position or form within the host cell in which the element is not ordinarily found in nature.

The term "recombinant", as used herein, refers to any gene or DNA segment that is introduced into a recipient cell, regardless of whether a similar gene might already be present in such a cell. The type of DNA included in the recombinant DNA can include DNA that is already present in the plant cell, DNA from another plant, DNA from a different organism, or a DNA generated externally, such as a DNA sequence containing an antisense message of a gene, or a DNA sequence encoding a synthetic or modified version of a gene.

The term "oxidative burst" refers to a plant defense response which involves the production of reactive oxygen species (ROS), such as the superoxide ion and hydrogen peroxide. It is the plant defense response that causes localized cell death, restricting pathogen spread.

The term "analog", as used herein, refers to a structural chemical derivative of a parent compound.

The term "oxidative stress inhibitors", as used herein, refers to any compound which modulates or inhibits any oxidative stress caused by any factor, including but not limited to a plant pathogen-induced oxidative burst and/or tissue culture-induced oxidative stress. Oxidative stress inhibitors encompass, but are not limited to, antioxidants.

The term "modulators", as used herein, refers to any compound which modulates in any way oxidative stress caused by any factor. Modulators may or may not be antioxidant compounds. Modulators may or may not be chemical derivatives of antioxidant compounds.

The term "positive effect", as used herein, refers to any increase in the efficacy of the transformation used. The positive effect may be as little as a fractional increase or may be an increase of several fold.

DETAILED DESCRIPTION

A major problem inherent in *Agrobacterium*-based transformation systems is that *Agrobacterium tumefaciens* causes a browning/necrosis response, likely the result of an oxidative burst, in the plant, plant tissue, or plant cells undergoing the transformation process. The browning/necrosis response can limit the regeneration frequency and thus the efficiency of transgenic plant production in several economically important crop species and varieties. The presently disclosed subject matter provides an improved transformation media by the addition of one or more compounds to the plant tissue culture that can increase transformation frequencies by reducing the effects of the oxidative burst, i.e. the tissue browning/necrosis response. The present invention provides an improved transformation media that has application to crops species and varieties that are recalcitrant or difficult to transform.

Many crops are transformed by inoculating plant tissue with *Agrobacterium tumefaciens;* maintaining these cultured cells on media for several weeks to effect selection for the growth of the rare, stably transformed cells; and then regenerating transgenic plantlets from the undifferentiated selected cells. One problem inherent in *Agrobacterium*-based transformation systems is that *Agrobacterium tumefaciens* is, despite being disarmed, a plant pathogen that causes an oxidative burst in co-inoculated plant cells of many species. In intact plants, the oxidative burst is a plant defense response that causes localized cell death, restricting pathogen spread. Due to the oxidative burst caused by *Agrobacterium* and other potential sources of oxidative stress, many commercially important plants are difficult to maintain in tissue culture during transformation, due to tissue browning and associated necrosis. Another problem is that many crop species (such as soybean) are difficult to regenerate, and shoot elongation is delayed or does not occur. Finally, in some transformation systems (such as soybean using selection on kanamycin and other selectable markers), a large proportion of the shoots regenerated are not transformants, but "shoot escapes" from selection. These three common problems in plant transformation—tissue browning/necrosis, recalcitrance to regeneration, and shoot escapes—can limit transgenic plant production using *Agrobacterium*-mediated transformation, with effects ranging from the moderate to the severe, depending on the crop and the cultivar in question.

The present invention includes the use of a compound or compounds which modulate oxidative burst, such as melatonin, 6-hydroxy melatonin (a melatonin analog), N-t-butyl hydroxylamine (NtBH), thiamazole, 1,3 dimethylthiourea, resveratrol, epicatechin, NADPH, or NADH, to enhance transformation efficiency. This list of compounds which modulate oxidative burst is intended to be exemplary and not comprehensive. Other compounds or modulators may be apparent to those skilled in the art and may be substituted here. By way of example and not limitation, at 10, 50 and 100 µM of melatonin in transformation media, tissue browning was reduced by 3.0, 5.5 and 10.2 fold, respectively (Table 3 and 4), in *Solanum lycopersicum* (tomato) compared to the negative control. The effect of melatonin on the frequency of generating independent stable transgenic events in tomato at 10, 50, 100, 500 and 1000 µM concentrations was investigated. Melatonin at the 10, 50 and 100 µM concentrations significantly (P<0.01) increased the frequency of independent stable transgenic events, from 88% (negative control without melatonin) to 229% (Table 3 and 4). Melatonin at 100 µM resulted in the highest reduction of tissue browning, and optimized transient expression and frequency of stable transgenic events. The inclusion of melatonin, 6-hydroxy melatonin (a melatonin analog), N-t-butyl hydroxylamine (NtBH), thiamazole, 1,3 dimethylthiourea, resveratrol, epicatechin, NADPH, or NADH has proved useful as an addition to media used for monocotyledonous and dicotyledonous plants at various steps throughout the transformation and regeneration process.

Thus it has been discovered that the inclusion of melatonin, 6-hydroxy melatonin (a melatonin analog), N-t-butyl hydroxylamine (NtBH), thiamazole, 1,3 dimethylthiourea, resveratrol, epicatechin, NADPH, or NADH in at least one plant transformation media during the transformation and/or regeneration process increases the efficiency of transformation of a plant explant with a selected nucleic acid fragment and/or the regeneration of a transgenic plant therefrom and the survivability of plant cells, tissue or other explant during the transformation process. Disclosed herein is the use of melatonin in the transformation media used for crops such as tomato, rice, and soybean.

The present invention also includes providing a method for introducing a nucleic acid sequence into the genome of a monocotyledonous or dicotyledonous plant, a monocotyledonous or dicotyledonous plant cell, or monocotyledonous or dicotyledonous plant tissue and regenerating a transformed plant therefrom, the method comprising culturing the plant cell on at least one plant transformation media, comprising an effective amount of a compound or compounds which modulate oxidative burst, such as melatonin, 6-hydroxy melatonin (a melatonin analog), N-t-butyl hydroxylamine (NtBH), thiamazole, 1,3 dimethylthiourea, resveratrol, epicatechin, NADPH, or NADH. An effective amount of melatonin in the transformation media is from about 1 µM to about 2000 µM. Another effective amount of melatonin in the transformation media is from about 5 µM to about 1500 µM. Still another effective amount of melatonin in the transformation media is from about 10 µM to about 100 µM.

As described in the examples below, melatonin may be added to plant transformation media at various individual steps or in one or more of the steps of the transformation process in different plant species to optimize its use for the particular plant species. Although not intending to be bound hereby, the inclusion of melatonin in a plant transformation media is beneficial during the stages of transformation and/or regeneration where the plant tissues are exposed to plant stress conditions. These media include but are not limited to inoculation media, co-cultivation media, selection media, and/or recovery media. These media are standard in transformation laboratories across the industry. Recipes for these media are well known to the skilled practitioner.

The amount of a compound or compounds which modulate oxidative burst to be included in the plant transformation media, and in which media during the transformation/regeneration process it should be included to be most efficacious, varies from plant species to plant species and with the transformation system being employed. For example, in an *Agrobacterium*-based MicroTom (a cultivar of tomato) transformation process (Dan, et al. 2006), melatonin has been beneficially included in the media, in concentrations from about 1-2000 µM, and also in concentrations from 10-100 µM. The melatonin can be derived from natural sources, or can be synthetic.

In accordance with the presently disclosed subject matter, melatonin analogs that provide the same function that melatonin does when used in accordance with this presently disclosed subject matter could also be used according to the present invention. A representative melatonin analog is 6-hydroxy melatonin. Other melatonin analogs would be apparent to one of ordinary skill in the art upon a review of the instant disclosure.

As described herein, the inclusion of a compound or compounds which modulate oxidative burst, such as melatonin, 6-hydroxy melatonin (a melatonin analog), N-t-butyl hydroxylamine (NtBH), thiamazole, 1,3 dimethylthiourea, resveratrol, epicatechin, NADPH, or NADH, in plant transformation media can advantageously be used with any plant, including dicotyledonous and monocotyledonous plants. Although various transformation systems are well known to those skilled in the art, a brief description of the process is provided below.

Typically, to initiate a transformation process in accordance with the presently disclosed subject matter, it is first desirable to select the genetic components desired to be inserted into the plant cells or tissues. Genetic components can include any nucleic acid that is introduced into a plant cell or tissue using the method according to the presently disclosed subject matter. Genetic components can include non-plant DNA, plant DNA, or synthetic DNA.

Approaches for preparing plasmids or vectors containing the desired genetic components are well known in the art. Vectors typically comprise a number of genetic components, including but not limited to regulatory elements such as promoters, leaders, introns, and terminator sequences. Regulatory elements are also referred to as cis- or trans-regulatory elements, depending on the proximity of the element to the sequences or gene(s) they control. These methods are well known to those of ordinary skill in the art and have been reported (see, for example, Sambrook et al., Molecular Cloning: A Laboratory Manual, Second Edition, Cold Spring Harbor Laboratory Press, Cold Spring Harbor, N.Y., 1989).

The present invention can be used with any suitable plant transformation plasmid or vector containing a selectable or screenable marker and associated regulatory elements as described, along with one or more nucleic acids (a structural gene of interest) expressed in a manner sufficient to confer a particular desirable trait. Examples of suitable structural genes of interest envisioned by the presently disclosed subject matter can include, but are not limited to, genes for insect or pest tolerance, herbicide tolerance, heterologous enzyme expression, genes for quality improvements such as yield, nutritional enhancements, environmental or stress tolerances, or any desirable changes in plant physiology, growth, development, morphology, or plant product(s).

Exemplary nucleic acids that can be introduced by the methods encompassed by the presently disclosed subject matter include, for example heterologous, exogenous, and/or recombinant nucleic acid sequences, as defined herein.

In light of the present disclosure, numerous other possible selectable or screenable marker genes, regulatory elements, and other sequences of interest will be apparent to those of ordinary skill in the art. Therefore, the foregoing discussion is intended to be exemplary rather than exhaustive.

Several technologies for the introduction of DNA into cells are well known to those of ordinary skill in the art and can be divided into categories including but not limited to: (1) chemical methods; (2) physical methods such as microinjection, electroporation and particle bombardment; (3) viral vectors; (4) receptor-mediated mechanisms; and (5) *Agrobacterium*-mediated plant transformation methods.

After the construction of the plant transformation vector or construct, the nucleic acid molecule, prepared as a DNA composition in vitro, is introduced into a suitable host such as *E. coli* and mated into another suitable host such as *Agrobacterium*, or directly transformed into competent *Agrobacteria*. These techniques are well-known to those of ordinary skill in the art and have been described for a number of plant systems including but not limited to corn (maize), soybean, rice, sugar beet, cotton, and wheat.

Those of ordinary skill in the art will recognize the utility of *Agrobacterium*-mediated transformation methods. Representative strains can include, but are not limited to, *Agrobacterium tumefaciens* strain C58, a nopaline strain that is used to mediate the transfer of DNA into a plant cell; octopine strains, such as LBA4404; or agropine strains, e.g., EHA101, EHA105, or EHA109. The use of these strains for plant transformation has been reported, and the methods are familiar to those of ordinary skill in the art.

The present invention can be used with any one or more regenerable cell or tissue. Those of ordinary skill in the art recognize that regenerable plant tissue generally refers to tissue that after insertion of exogenous DNA and appropriate culture conditions can form into a differentiated plant. Such tissue can include, but is not limited to, callus tissue, hypocotyl tissue, cotyledons, meristematic tissue, roots, and/or leaves. For example, regenerable tissues can include calli or embryoids from anthers, microspores, inflorescences, and/or leaf tissues. Other tissues are also envisioned to have utility in the practice of the presently disclosed subject matter, and the desirability of a particular explant for a particular plant species is either known in the art or can be determined by routine screening and testing experiments after a review of the presently disclosed subject matter, whereby various explants are used in the transformation process and those that are more successful in producing transgenic plants are identified.

Once the regenerable plant tissue is isolated, the genetic components can be introduced into the plant tissue. This process is also referred to herein as "transformation". The plant cells are transformed and each independently transformed plant cell is selected. The independent transformants are referred to as plant cell lines or "events".

Methods for transforming dicots, primarily by use of *Agrobacterium tumefaciens*, and obtaining transgenic plants have been published for a number of crops including cotton, soybean, *Brassica*, and peanut.

Successful transformation of monocotyledonous plants describing the use of electroporation, particle bombardment, and/or *Agrobacterium* based methods have also been reported. Transformation and plant regeneration have been achieved and reported at least in asparagus, barley, maize, oat, rice, tall fescue, wheat, and sugarcane.

The present invention finds use in *Agrobacterium*-mediated transformation processes. *Agrobacterium*-inoculated explants are typically cultured on an appropriate co-culture medium to allow for transfer of the genetic component containing the gene-of-interest to be introduced into the plant cells/tissue for incorporation into its genome. Appropriate co-culture media is typically known for each culture system or can be determined by one of ordinary skill in the art. In accordance with the present invention, the co-culture media contains an effective amount of a compound or compounds which modulate oxidative burst, such as melatonin, 6-hydroxy melatonin (a melatonin analog), N-t-butyl hydroxylamine (NtBH), thiamazole, 1,3 dimethylthiourea, resveratrol, epicatechin, NADPH, or NADH.

*Agrobacterium*-inoculated explants are typically cultured on an appropriate medium containing an agent to inhibit *Agrobacterium* growth. This media is usually referred to as a delay media or a selection media. The *Agrobacterium*-inoculated explants are cultured on such a media generally from one to fourteen days, preferably from two to seven days. Those of ordinary skill in the art are aware of the appropriate media components to inhibit *Agrobacterium* growth. Such media components would include, but are not limited to, antibiotics such as carbenicillin or cefotaxime.

After the culture step to inhibit *Agrobacterium* growth, and optimally before the explants can be placed on selective media, they can be analyzed for efficiency of DNA delivery by a transient assay that detects the presence of a gene contained on the transformation vector, including, but not limited to, a marker gene such as the gene that codes for β-glucuronidase (GUS). The total number of blue spots (indicating GUS expression) for a selected number of explants is used as a positive correlation of DNA transfer efficiency.

The present invention can include, after incubation on non-selective media containing the antibiotics to inhibit *Agrobacterium* growth without selective agents (delay medium), the explants are cultured on selective growth media including, but not limited to, a callus-inducing media containing a selective agent. Typical selective agents have been described and include, but are not limited to, antibiotics such as geneticin (G418), paromomycin, kanamycin, or other chemicals such as glyphosate. Delay media or selection media can also contain an effective amount of melatonin or an analog thereof. The plant tissue cultures surviving the selection media are subsequently transferred to a regeneration media suitable for the production of transformed plantlets. Regeneration can be carried out over several steps. Regeneration media at any step can contain an effective amount of a compound or compounds which modulate oxidative burst, such as melatonin, 6-hydroxy melatonin (a melatonin analog), N-t-butyl hydroxylamine (NtBH), thiamazole, 1,3 dimethylthiourea, resveratrol, epicatechin, NADPH, or NADH. Those of ordinary skill in the art are aware of the numerous types of media and transfer requirements that can be implemented and optimized for each plant system for plant transformation and regeneration. Consequently, such media and culture conditions disclosed herein can be modified or substituted with nutritionally equivalent components, or similar processes for selection and regeneration, and still fall within the scope of the presently disclosed subject matter.

The transformants produced are subsequently analyzed to determine the presence or absence of a particular nucleic acid of interest contained on the transformation vector. Molecular analyses can include, but are not limited to, Southern blots (Southern, Mol. Biol., 98:503-517, 1975) or PCR (polymerase chain reaction) analyses. These and other well known methods can be performed to confirm the stability of the transformed plants produced by the methods disclosed. These methods are well known to those of ordinary skill in the art and have been reported (see, for example, Sambrook et al., Molecular Cloning: A Laboratory Manual, Second Edition, Cold Spring Harbor Laboratory Press, Cold Spring Harbor, N.Y., 1989).

The previous discussion is merely a broad outline of standard transformation and regeneration protocols. One of ordinary skill in the art knows that specific crops and specific protocols can vary somewhat from the broad outline. A variety of media can be used in each system as well. Those of ordinary skill in the art are familiar with the variety of tissue culture media that, when supplemented appropriately, support plant tissue growth and development. These tissue culture media can either be purchased as a., commercial preparation or custom prepared and modified by those of ordinary skill in the art. Examples of such media would include, but are not limited to, Murashige and Skoog (Murashige and Skoog, Physiol. Plant, 15:473-497, 1962), N6 (Chu et al., Scientia Sinica 18:659, 1975), Linsmaier and Skoog (Linsmaier and Skoog, Physio. Plant., 18: 100, 1965), Uchimiya and Murashige (Uchimiya and Murashige, Plant Physiol. 15:473, 1962), Gamborg's media (Gamborg et al., Exp. Cell Res., 50:151, 1968), D medium (Duncan et al., Planta, 165:322-332, 1985), McCown's Woody plant media (McCown and Lloyd, Hort-Science 16:453, 1981), Nitsch and Nitsch (Nitsch and Nitsch, Science 163:85-87, 1969), and Schenk and Hildebrandt (Schenk and Hildebrandt, Can. J. Bot. 50:199-204, 1972) or derivations of these media supplemented accordingly. Those of ordinary skill in the art are aware that media and media supplements such as nutrients and growth regulators for use in transformation and regeneration are usually optimized for the particular target crop or variety of interest. See Table 1 for a list of exemplary media wherein the addition of an oxidative stress modulator can have a positive effect.

TABLE 1

Types of Media useful in transformation protocols

Callus Induction
Cocultivation
Co-culture
D medium
Delay
Elongation
Fillatti's Suspension Medium
Gamborg's Media
Germination
Induction
Infection
Inoculation
Linsmaier and Skoog
McCown's Woody Plant Media
Murashige and Skoog
N6
Nitsch and Nitsch
Recovery
Regeneration
Rooting
Schenk and Hildebrandt
Selection
Uchimiya and Murashige

EXAMPLES

The following examples further illustrate the presently disclosed subject matter. They are in no way to be construed as a limitation in scope and meaning of the claims.

Example 1

Tomato Transoformation Media Using Melatonin

Tomato transformation techniques are known in the art and are described in Dan, et al. 2006 and US Patent Application No: US2004/0133938A1

Germination.
Day 1 between 4:00 to 5:00 pm.
1. Sterilize MicroTom tomato seeds: (2.1 grams (g) of MicroTom tomato seeds, which equals approximately 900 seeds; supplied by Ball Horticultural Company, Chicago, Ill., USA.
add approximately 900 seeds to a sterile 250 milliliter (ml) flask
soak for 10 minutes (min) in the sterile 250 ml flask with ~100 ml sterile double deionized (dd) water and then pour off the water.
add 100 ml of 70% ethanol to immerse the seeds for 1 min while stirring vigorously, pour off the ethanol, rinse the seeds 2 times with sterile dd water.
soak the seeds in 100 ml of 25% Chlorine bleach solution (chlorine bleach available under the registered trademark CLOROX®) with 3 drops of TWEEN™ 20 detergent for 10 min while stirring frequently, rinse the seeds three times with sterile dd water.
the seeds are germinated in MAGENTA™ box (available from bio-WORLD, Dublin, Ohio, United States of America) or culture box containing TGM medium (approximately 70 seeds/container), and the MAGENTA™ boxes are placed in a plastic box that is wiped down with 70% ethanol. The box cultures are placed in a dark incubator at 27° C. under the dark for 6 days (d). Seeds are distributed evenly and closely in the MAGENTA™ box, and pressed down on the media surface when placing the seeds on the germination medium.
Day 6 at 12:00 pm.
The box cultures are transferred to growth incubator and cultured at 24° C. and a 16-hour (h) photoperiod with a light intensity of approximately 15 micromoles per meter$^2$ per second ($\mu mol \cdot m^2 \cdot sec$) for about 26 h.
Construct Information: The construct used in transformation contains a CaMV 35S promoter driving GUS (with GUS intron) and Nos promoter driving NPTII in Bin 19 binary vector (Frisch et al., 1995, Plant Molecular Biology 27:405-409). *Agrobacterium tumefaciens* strain EHA101 is used for transformation.
*Agrobacterium* Preparation.
150 microliters (μl) of Vector 1 glycerol stock from −80° C. are placed on a fresh Luria Broth (LB)/rifampicin 50 microgram (μg)/ml/kanamycin 50 μg/ml plate on Friday of the week before transformation experiment, grown at about 28° C. for 3-4 d and stored in the refrigerator (4° C.) for the rest of the week. One day before inoculation, between 1:00 to 2:00 pm, a loopful of the bacterium cells from the freshly streaked plate is inoculated into 2 ml of liquid LB/rifampicin 50 μg/ml/kanamycin 50 μg/ml in a 17×100 Falcon tube, and grown at 28 C.° with 230 revolutions per minute (rpm) shaking. The next morning between 8:00 to 9:00 am, 0.2 ml of the overnight bacterium culture is inoculated into 2 ml of plain LB+0.2 millimeter (mM) acetosyringone in a 17×100 mm Falcon tube, and grown at about 28° C. with 230 rpm for 4 h.
Explant Preparation.
Day 7 at about 2:00 pm.
1) Cotyledon explants are isolated from seedlings 6 d after sowing seeds on TGM medium.
2) About 25 cotyledon explants are prepared at a time by bathing them in a sterile petri dish plate containing 6 ml of Fillatti' s suspension medium (FSM) liquid medium to prevent desiccation and trimming them at both ends using a #15 feather blade. Note: it is desirable to use the cotyledons that make a fairly tight "V" shape (two cotyledons that are at closed shape are acceptable to be used).

3) Immediately after the trimming, the 25 cotyledon explants are gently placed on "feeder plates"—TCM medium. The "feeder plates" are made by overlaying 2 ml of tobacco suspension cells and a sterile WHATMAN™ filter (No. 1, Cat No. 1001090, VWR; Whatman Inc., Florham Park, N.J., United States of America) on the plates containing TCM medium.

4) Cotyledon explants are gently poked with a sharp forceps and usually six pokes are made per explant. It is desirable that the sharp forceps gently touch the surface of explants and then make a slight movement on the touched surface in order to have a larger and shallower wounding surface that results in good transient expression.

5) Right after poking, the cotyledons are inoculated with Agrobacterium by adding 3 ml of the Agrobacterium solution ($OD_{600}$=0.1) suspended in FSM liquid medium to the top of cotyledons. The plates are incubated for 10 min at room temperature and the Agrobacterium solution is aspirated with a sterile pipette. The cotyledons are then co-cultured for 2 d at 24° C. and a 16 h photoperiod with a light intensity of approximately 15 $\mu mol \cdot m^2 \cdot sec$. The co-culture plates are placed in plastic bags to retain humidity, which favors MicroTom tomato growth.

Regeneration (100×25 mm Plates).

Shoot induction under selection.

Two days after co-cultivation cotyledons are transferred to TSM selective medium supplemented with 100 μM melatonin and cultured at 23-24° C. and under a 16 h photoperiod with a light intensity of approximately 15 $\mu mol \cdot m^2 \cdot sec$. The co-culture plates are placed inside of plastic boxes covered with plastic bags to retain humidity; which favors MicroTom tomato growth.

Data Collection.

For tissue browning and transient expression data collection, 3 d after selection cotyledon explant data are collected for tissue browning under a dissecting microscope, and then for transient expression by GUS staining.

For data collection of the stable transformation frequency (T.F. (%)=(number of independent transgenic calli/buds that expressed GUS÷number of total explants)×100%), approximately four weeks after selection cotyledon explants with calli/buds are assayed by GUS staining; only one callus/bud expressing GUS from each pock is counted as a transgenic event.

| Melatonin Stock Solution. | |
| --- | --- |
| Chemical: | Melatonin |
| Code: | Compound A |
| Synonym: | N-Acetyl-5-methoxytryptamine |
| Molecular Formula: | $C_{13}H_{16}N_2O_2$ |
| Molecular weight: | 232.28 |
| Order Information: | Sigma-Aldrich, PO Box 14508, St. Louis, Missouri, United States of America 63178, 800.325.3010, Cat. No.: M5250. |
| Storage of powder: | −20° C. |
| Solubility: | 8 mg/ml to 46.46 mg/ml using 95% ethanol (information from Sigma-Aldrich technical representative and experiment tests). |
| Caution: | Solutions are light sensitive and subject to oxidation. |

Stock concentrations that were used:

For the first set of experiments testing melatonin at 10, 50 and 100 μM, 8 mg/ml of the stock solution was used.

For the second set of experiments testing melatonin at 100, 500 and 1000 μM, 46.46 mg/ml (200 mM) of the stock solution was used.

Protocol for 8 mg/ml Stock Prep:

For 10 ml stock solution:

1. Weigh 80 mg melatonin on weigh paper on analytical balance.
2. Carefully transfer powder to a 25 or 50 ml beaker, add 5 ml 95% ethanol, mix gently to dissolve. When fully dissolved bring volume to 10 ml using a graduate cylinder and 95% ethanol.
3. Filter-sterilize the solution under sterile conditions.
4. Transfer 1 ml aliquots to sterile cry-tubes under sterile conditions.
5. Label caps with A, label side with 8 mg/ml and the date.
6. Store the tubes in a −20° C. freezer.

Protocol for 46.46 mg/ml (200 mM) Stock Prep:

For 5 ml stock solution:

1. Weigh 232.3 mg melatonin on weigh paper on an analytical balance.
2. Carefully transfer powder to a 25 or 50 ml beaker, add 4 ml 95% ethanol, mix gently to dissolve. When fully dissolved bring volume to 5 ml using a graduate cylinder and 95% ethanol.
3. Filter-sterilize the solution under sterile conditions.
4. Transfer 1 ml aliquots to sterile cry-tubes under sterile conditions.
5. Label caps with A, label side with 200 mM and the date.
6. Store the tubes in a −20° C. freezer.

TABLE 2

Tomato transformation media used

| Component | Co-culture | Germination |
| --- | --- | --- |
| MS basal salts | 2.2 g/l | 4.3 g/l |
| Thiamine | 0.9 mg/l | — |
| KH2PO4 | 0.2 g/l | — |
| Sucrose | 30 g/l | 20 g/l |
| 2,4-Dichlorophenoxyacetic acid | 0.2 mg/l | — |
| 4-Chlorophenoxyacetic acid | 4 mg/l | — |
| Kinetin | 0.1 mg/l | — |
| Agar | 10 g/l | 8 g/l |
| Acetosyringone | 39.3 mg/l | — |
| D-(+)-Galacturonic acid monohydrate | 212.2 mg/l | — |
| Gamborg's Vitamins | — | 1 mg/l |
| pH | 5.8 | 5.8 |
| 3-Indoleacetic acid | — | — |
| Zeatin riboside | — | — |
| Carbenicillin | — | — |
| Cefotaxime | — | — |
| Kanamycin | — | — |

| Component | Selection | FSM |
| --- | --- | --- |
| MS basal salts | 4.3 g/l | 4.3 g/l |
| Thiamine | — | — |
| KH2PO4 | — | — |
| Sucrose | 30 g/l | 30 g/l |
| 2,4-Dichlorophenoxyacetic acid | — | — |
| 4-Chlorophenoxyacetic acid | — | 4 mg/l |
| Kinetin | — | 5 ug/l |
| Agar | 8 g/l | — |
| Acetosyringone | — | — |
| D-(+)-Galacturonic acid monohydrate | — | — |
| Gamborg's Vitamins | 1 mg/l | 1 mg/l |
| pH | 5.8 | 5.8 |
| 3-Indoleacetic acid | 0.1 mg/l | — |
| Zeatin riboside | 2 mg/l | — |

TABLE 2-continued

Tomato transformation media used

| Carbenicillin | 500 mg/l | — |
|---|---|---|
| Cefotaxime | 100 mg/l | — |
| Kanamycin | 100 mg/l | — |

Media listed in Table 2 are prepared in 1 Liter batches.

TABLE 3

Effect of 10, 50 and 100 µM melatonin in selection stage media on tissue extreme browning severity of MicroTom tomato cotyledons 3 days after explants were first cultured on selection media.

| Treatment | Extreme[X] Browning Rate | Fisher's LSD[Y] |
|---|---|---|
| Negative control (0 melatonin) | 64.8% | A |
| 10 µM melatonin | 21.5% | C |
| 50 µM melatonin | 11.8% | BC |
| 100 µM melatonin | 6.4% | B |

[X]Extreme browning rate defined as percentage of pokes having a browning area of ≧70%.

[Y]Treatments with different letters are significantly different (p < 0.05) using Fisher's LSD test (K. A. Gomez & A. A. Gomez, Statistical Procedures for Agricultural Research, 2nd edition, John Wiley & Sons; Kirk, R.E. 1982. Experimental Design (Second Ed.): Procedures for the Behavioral Sciences, p115, Brooks/Cole Pub. Co.).

TABLE 4

Effect of 100, 500 and 1000 µM melatonin on tissue extreme browning rate of MicroTom tomato cotyledons 3 days after selection.

| Treatment | Extreme[X] Browning Rate | Fisher's LSD[Y] |
|---|---|---|
| Negative control (0 melatonin) | 73.6% | A |
| 100 µM melatonin | 22.2% | C |
| 500 µM melatonin | 21.0% | C |
| 1000 µM melatonin | 50.6% | B |

[X]Extreme browning rate defined as percentage of pokes with a browning area of ≧70%.
[Y]Treatments with different letters are significantly different (p < 0.05) using Fisher's LSD test. Melatonin at 100, 500 and 1000 µM highly significantly (p < 0.05) reduced extreme tissue browning (extreme browning defined as more than 70% of poked area being brown) than the negative control. The relative reductions were 3.3, 3.5 and 1.4 fold for 100, 500 and 1000 µM melatonin, respectively.

TABLE 5

Effect of 10, 50 and 100 µM melatonin on frequency of independent stable transgenic events and escapes 4 weeks after selection, in MicroTom transformation.

| Treatment | Frequency of independent stable transgenic events (%)[Y] | Frequency of escapes (%) |
|---|---|---|
| Negative control (no melatonin) | 88.1% ± 25.6 B | 11.7 ± 2.4 |
| Melatonin at 10 µM | 214.4% ± 6.2 A | 1.7 ± 0.0 |
| Melatonin at 50 µM | 221.3% ± 47.7 A | 0.0 ± 0.0 |
| Melatonin at 100 µM | 229.4% ± 55.7 A | 0.0 ± 0.0 |

[Y]Treatments with different letters are significantly different (p < 0.05) using Fisher's LSD test. Melatonin at 10, 50 and 100 µM significantly (p < 0.05) increased the frequency of independent stable transgenic events compared with the negative control. Melatonin at 10, 50 and 100 µM dramatically reduced the frequency of escapes from 11.7% in the negative control to 1.7%, 0% and 0%, respectively.

TABLE 6

Effect of 100, 500 and 1000 µM melatonin on the frequency of independent stable transgenic events 4 weeks after selection, in MicroTom transformation.

| Treatment | Frequency of independent stable transgenic events (%)[Y] |
|---|---|
| Negative control | 106.7% ± 23.6 B |
| Melatonin at 100 µM | 213.3% ± 75.4 A |
| Melatonin at 500 µM | 121.7% ± 1.7 B |
| Melatonin at 1000 µM | 80.0% ± 14.1 B |

[Y]Treatments with different letters are significantly different (p < 0.05) using Fisher's LSD test. Melatonin at 100 µM significantly (p < 0.05) increased the frequency of independent stable transgenic events compared with the negative control. The rate of increase was 2.0 fold.

Oxidative Stress Inhibitors Enhancing Transformation in MicroTom

The frequencies of independent stable transgenic events were significantly (P<0.01) higher than that of a negative control when using N-t-butyl hydroxylamine at concentrations of 10, 50 and 100 µM (Table 7). N-t-butyl hydroxylamine at 10 µM significantly (P<0.01) increased the frequency of independent stable transgenic events compared with the negative control and reduced the frequency of escapes by 2.5 fold compared with the negative control (Table 7).

TABLE 7

Effect of 10, 50 and 100 µM N-t-butyl hydroxylamine on the frequencies of independent stable transgenic events and escapes 4 weeks after selection, in MicroTom transformation.

| Treatment | Frequency of independent stable transgenic events (%)[Y] | Frequency of escapes (%) |
|---|---|---|
| Negative control (no N-t-butyl hydroxylamine) | 121.1 ± 13.5 C | 11.1 ± 6.9 |
| N-t-butyl hydroxylamine (10 µM) | 245.6 ± 44.0 A | 4.4 ± 5.1 |
| N-t-butyl hydroxylamine (50 µM) | 222.2 ± 9.6 AB | 6.7 ± 3.3 |
| N-t-butyl hydroxylamine (100 µM) | 205.6 ± 10.2 AB | 8.9 ± 1.9 |

[Y]The treatments with different letters represent highly significantly (P < 0.01) differences using Fisher's LSD test.

The oxidative stress inhibitor resveratrol at a concentration of 100 µM highly significantly (P<0.01) increased the frequency of independent stable transgenic events compared with a negative control. At the same concentration, it reduced escapes 5-fold compared with the negative control (Table 8).

TABLE 8

Effects of 50, 100 and 200 µM resveratrol on the frequencies of independent stable transgenic events and escapes 6 weeks after selection, in MicroTom transformation.

| Treatment | Frequency of independent stable transgenic events (%)[Y] | Frequency of escapes (%) |
|---|---|---|
| Negative control (no resveratrol) | 267.8 ± 10.2 BC | 5.6 ± 3.8 |
| Resveratrol (50 µM) | 297.8 ± 24.6 B | 4.4 ± 7.7 |
| Resveratrol (100 µM) | 356.7 ± 10.0 A | 1.1 ± 1.9 |
| Resveratrol (200 µM) | 227.8 ± 17.1 C | 1.1 ± 1.9 |

[Y]The treatments with different letters represent highly significantly (P < 0.01) different using Fisher's LSD test.

Another oxidative stress inhibitor, epicatechin at a concentration of 100 mg/l had a highly significant (P<0.01) effect in increasing the frequency of independent stable transgenic events compared with a negative control (Table 9). At the same concentration, it reduced the frequency of escapes from 6.7% in the negative control to 0% (Table 9). Epicatechin highly significantly (P<0.01) reduced the stable transformation frequency compared with the negative control at the concentration of 1000 mg/l, indicating that it might be toxic to plant tissues at that concentration (Table 9).

TABLE 9

Effects of 50, 100 and 1000 mg/l epicatechin on the frequencies of independent stable transgenic events and escapes 6 weeks after selection, in MicroTom transformation.

| Treatment | Frequency of independent stable transgenic events (%)$^Y$ | Frequency of escapes (%) |
|---|---|---|
| Negative control (no epicatechin) | 226.7 ± 4.7 C | 6.7 ± 0.0 |
| Epicatechin (50 mg/l) | 418.3 ± 25.9 B | 1.7 ± 2.4 |
| Epicatechin (100 mg/l) | 521.7 ± 16.5 A | 0.0 ± 0.0 |
| Epicatechin (1000 mg/l) | 51.7 ± 2.4 D | 1.7 ± 2.4 |

$^Y$The treatments with different letters represent highly significantly (P < 0.01) differences using Fisher's LSD test.

Example 2

Rice Transformation Media Using Melatonin

Mature Seed Sterilization.
1. Dehusk seeds and remove seeds with brown or dark spots (suggests fungal infection). Check for any off-type seeds and discard these.
2. Surface sterilize seeds in a 50 ml sterile tube with 70% ethanol for 1 to 2 min with shaking (ethanol treatment step is optional).
3. Remove ethanol.
4. Add 50% (v/v) CLOROX® bleach (2.4% Na hypochlorite) or 40% (v/v) ULTRA CLOROX® (~3.2% Na hypochlorite) and one drop of TWEEN™-20 detergent, shake for 30-40 min on a shaker at 100-200 rpm.
5. Remove CLOROX® solution and rinse with sterile water at least three times, until all sign of TWEEN™-20 detergent (soap bubbles) is gone.
6. Seeds are ready to plate on sterile medium.
7. Check for bacterial and fungal contaminations at 3 and 5 days later, respectively.

Target Tissue Production.
1. Soak sterilized seeds in sterile water for 1-2 d until fully imbibed (optional step)
2. Plate pre-soaked or sterilized mature seeds onto rice callus induction medium (MS-CIM) at 12 seeds per plate. Culture in dark at 28° C. for 6 d prior to inoculation or for 4 weeks (wks) for production of embryogenic cultures.
3. At 4 wks, selectively excise high quality target material and transfer to MS-CIM at 25 pieces per plate. Culture in dark for 8 d at 28° C. before inoculation.

Rice Transformation.
Inoculation:
1. If possible, choose bacteria from the area of the plate where there are many individual single colonies of bacteria growing for inoculation. Transfer ~7 inoculation loops full of *Agrobacterium* culture to a 50 ml sterile plastic tube containing 20 ml liquid MS media with acetosyringone (As) added to 200 μM (add 1 μl As stock at 40 mg/ml per ml of suspension). Vortex to completely dissolve bacteria in liquid and bring volume to 50 ml.
2. Measure the *Agrobacterium* suspension OD at 660 nm. Dilute the culture to an OD660 of 0.2-0.3 (higher concentrations can offer higher transformation frequencies but can cause damage/browning in some cultivars). Induce the bacteria with acetosyringone for at least 30 min.
3. Inoculate cultured rice seeds or rice embryogenic culture responses by immersing target material in the bacterial suspension for 30 min.
4. Try to make sure that all target pieces are completely immersed in the bacterial solution and shake regularly to ensure that this continues to be the case.
5. Use a vacuum aspirator apparatus to remove the liquid *Agrobacterium* suspension from responding seeds/cultures.

Genotype: Nipponbare Calli: 7 days after subculture
Construct: 12672
Agro OD: 0.4
Total Calli: 300 (50 per treatment)
MT=Melatonin
Agro Suspension made in each melatonin concentration
A: Inoculation media
B: Inoculation media+2MT
C: Inoculation media+10MT
D: Inoculation media+100MT
E: Inoculation media+300MT
F: Inoculation media+1000MT
Above concentrations in μM Co-Cultivation.
Transfer the inoculated seeds/cultures to multiple shoot-acetosyringone (MS-As) co-cultivation medium with sterile 85 mm filter paper. Each filter paper is wetted with 1 ml of MSInoc (see recipe below) liquid media with the concentrations of MT (in μM) listed below. Fifty (50) pieces per plate; incubate at 22° C. for 3 d.
A: Filter Paper
B: Filter Paper 2MT
C: Filter Paper 10MT
D: Filter Paper 100MT
E: Filter Paper 300MT
F: Filter Paper 1000MT Recovery.
1. After ~36 hours of co-cultivation, transfer the co-cultivated seeds/responses to *Agrobacterium* inhibition medium MS-400Tim (see recipe below) (1 plate→1 plate). Culture in the dark at 28° C. for ~7 days.
2. Score the scorable marker control plate for gene delivery efficiency at 4 to 5 days after co-cultivation
A: Recovery Media
B: Recovery Media+2MT
C: Recovery Media+10MT
D: Recovery Media+100MT
E: Recovery Media+300MT
F: Recovery Media+1000MT Selection.
1. Transfer calli to selection medium (17.5 g/l mannose/5 g/l sucrose). Culture in dark at ~28° C. for 2 to 3 weeks, observing periodically for colony proliferation and contamination.
2. Select mannose resistant embryogenic micro-colonies under microscope when proliferating colonies are big enough to grow independently, but not so big that they have begun to grow together. Excise the unique micro-colonies individually, transferring to ZeaMan20CuRegen regeneration induction/selection medium (see recipe below) (10 events per plate) and culture in the dark for another 2 weeks. Care in separating individual colonies arising from different transgenic cells on the same original culture piece can maximize the number of transgenic events produced. Score for number of stable events generated in the scorable marker control plate and the number of resistant micro-colonies (events) arising from each treatment.

Regeneration.

1. After 2 weeks of regeneration induction in the dark, transfer proliferating colonies (selecting for the more differentiated portions of colonies if possible) to Zea10ManRegen regeneration induction/selection medium (see recipe below) (5 colonies per plate) and move cultures to ~30° C. in light (16 h light/8 h dark).
2. When shoots are pushing up the plate lids (usually within 2 weeks), excise a single individual shoot from each event and transfer to rooting media (see recipe below) (4 events per rooting container).

Transfer to soil in the greenhouse after ~2 weeks, when plants are beginning to touch the top of the rooting container and an adequate root system is evident.

Experiments were conducted with 50 explants per treatment of melatonin concentration.

TABLE 10

Effect of melatonin concentration on rice stable callus transformation efficiency*.

| | Melatonin concentration | | | | | |
|---|---|---|---|---|---|---|
| | 0 μM | 2 μM | 10 μM | 100 μM | 300 μM | 1000 μM |
| % of stable callus sectors | 136.0% | 148.0% | 156.0% | 140.0% | 140.0% | 86.0% |

*Data collected from analysis of transgenic callus after selection

TABLE 11

Rice transformation media used in this invention

| Component | Inoculation | Callus Induction | Co-culture |
|---|---|---|---|
| MS Basal salts | 4.3 g/l | 4.3 g/l | 4.3 g/l |
| B5 Vitamins 200x | 5 ml | 5 ml | 5 ml |
| Sucrose | 20 g/l | 20 g/l | 20 g/l |
| Casein Hydrolate Enzymatic | 0.3 g/l | 0.3 g/l | 0.3 g/l |
| Glutamine | 0.5 g/l | 0.5 g/l | 0.5 g/l |
| Proline | 0.5 g/l | 0.5 g/l | 0.5 g/l |
| 2,4-Dichlorophenoxyacetic acid 1 mg/ml | 2 ml | 2 ml | 2 ml |
| Phytagel | — | 3 g/l | 3 g/l |
| pH | 5.8 | 5.8 | 5.8 |
| Acetosyringone 40 mg/ml | — | — | 1 ml |
| Ticarcillin 100 mg/ml | — | — | — |
| Mannose 1 g/ml | — | — | — |
| MES 100 mg/ml | — | — | — |
| CuSO4 5 mg/ml | — | — | — |
| Sorbitol | — | — | — |
| IAA 1 mg/ml | — | — | — |
| Zeatin, trans 5 mg/ml | — | — | — |

| Component | Recovery | Selection | Regeneration ZeaMan10Regen |
|---|---|---|---|
| MS Basal salts | 4.3 g/l | 4.3 g/l | 4.3 g/l |
| B5 Vitamins 200x | 5 ml | 5 ml | 10 ml |
| Sucrose | 20 g/l | 20 g/l | — |
| Casein Hydrolate Enzymatic | 0.3 g/l | 0.3 g/l | — |
| Glutamine | 0.5 g/l | 0.5 g/l | — |
| Proline | 0.5 g/l | 0.5 g/l | — |
| 2,4-Dichlorophenoxyacetic acid 1 mg/ml | 2 ml | 2 ml | — |
| Phytagel | 3 g/l | 3 g/l | 2 g/l |
| pH | 5.8 | 5.8 | 5.8 |
| Acetosyringone 40 mg/ml | — | — | — |
| Ticarcillin 100 mg/ml | 4 ml | 4 ml | 2 ml |
| Mannose 1 g/ml | — | 17.5 ml | 10 ml |
| MES 100 mg/ml | — | — | 5 g |
| CuSO4 5 mg/ml | — | — | 2.5 g |
| Sorbitol | — | — | 30 g/l |
| IAA 1 mg/ml | — | — | 0.5 g |
| Zeatin, trans 5 mg/ml | — | — | 0.2 ml |

| Component | Regeneration ZeaMan20Regen | Rooting |
|---|---|---|
| MS Basal salts | 4.3 g/l | 4.3 g/l |
| B5 Vitamins 200x | 10 ml | 10 ml |
| Sucrose | — | 20 g/l |
| Casein Hydrolate Enzymatic | — | — |
| Glutamine | — | — |
| Proline | — | — |
| 2,4-Dichlorophenoxyacetic acid 1 mg/ml | — | — |
| Phytagel | 2 g/l | 3.5 g/l |
| pH | 5.8 | 5.8 |
| Acetosyringone 40 mg/ml | — | — |
| Ticarcillin 100 mg/ml | 2 ml | 2 ml |
| Mannose 1 g/ml | 20 ml | — |
| MES 100 mg/ml | 5 g | — |
| CuSO4 5 mg/ml | 2.5 g | — |
| Sorbitol | 30 g/l | 20 g/l |
| IAA 1 mg/ml | 0.5 g | — |
| Zeatin, trans 5 mg/ml | 0.2 ml | — |

Media listed in Table 11 are prepared in 1 Liter batches.

Example 3

Soybean Transformation Media Using Melatonin

Purpose:

To examine the effect of melatonin on organogenic soybean transformation system, melatonin is applied in early stage of transformation procedure (from infection to co-cultivation).

Basic Parameters:

1) Three different concentrations of melatonin all applied to soybean transformation (0, 1, 10, 100 μM).
2) Melatonin is dissolved in DMSO.
3) Final concentration of DMSO in the soybean culture medium is less than 0.03%.
4) Selection: glyphosate resistance.

Procedure:

1) Soybean (*Glycine max*, Jack) stock plants all grown in greenhouse. Pods are collected and sterilized by immersing in 10-20% CLOROX® bleach and rinsing with sterile tap water. The isolated seeds are further sterilized with 5-10% CLOROX® bleach and followed by rinsing with sterile water. Sterilized seeds are used for preparing explants for *Agrobacterium*-mediated transformation.
2) The construct used for transformation contains a selectable marker for glyphosate resistance. *Agrobacterium tumefaciens* strain EHA101 is used for transformation. For plant transformation *Agrobacterium* cells are collected and suspended in liquid infection medium. Light absorption of the bacterial suspension is measured in a spectrophotometer and diluted to $A_{660}$ of 0.65±0.15. Acetosyringone is added to a final concentration of 40-80 mg/L (200-400 µM) to induce virulence gene expression.

3) Preparation of Immature Seed Transformation Targets: hypocotyl is trimmed off and the seed coat is removed. Cotyledon explants with the epicotyl are prepared by removing one of the cotyledons. Alternatively, immature seeds can be split into two halves along the embryo axis. The primary leaves are removed from the cotyledon explants with the blunt end of the scalpel. The region containing the apical meristem and the cotyleonary node is further wounded with the sharp end of blade gently, preferably 5-7 times.

4) Infection and Co-cultivation of Soybean Seed Explants: the prepared explants are immediately infected with *Agrobacterium* by mixing the isolated immature seed explants with bacterial suspension containing designated concentration of melatonin (0, 1, 10 and 100 µM). The mixture is incubated for 3 h at room temperature. Following infection, the explants are removed from the *Agrobacterium* suspension and placed on a co-cultivation medium containing designated concentration of melatonin (0, 1, 10 and 100 µM). The co-cultivation plates are incubated for 3 to 5 days at 22±1° C. in the dark.

5) Regeneration and Selection of Transgenic Plants: after co-cultivation, the explants are transferred to recovery medium (recipe below) without a selection agent and with appropriate antibiotics to inhibit *Agrobacterium* growth. The plates with the explants are incubated for about one week at 24° C. under a 16 h light/8 h dark regimen. After the recovery period, explants are transferred to regeneration media containing a selection agent and antibiotics (recipe below). After about 2-3 weeks in regeneration/selection media, developing multiple shoots clusters are excised and transferred to elongation medium (recipe below) containing an appropriate selection agent and antibiotics for shoot elongation. Subcultures to fresh elongation media are performed every 2-4 weeks until shoots are long enough to be transferred into soil. Dead leaves and tissue are removed during the sub-culturing steps.

6) Rooting, TAQMAN® assay: Elongated shoots (>3 cm) are transferred to moist soil in small pots directly and incubated in growth chamber for about 2 weeks. After 2 weeks, leaves were sampled for TAQMAN® analysis to identify plants positive for gene-of-interest.

Number of TAQMAN® positive plants were counted and analyzed to generate transformation efficiency data.

TABLE 12

Effect of melatonin on soybean transformation frequency*

| | Melatonin concentration | | | |
|---|---|---|---|---|
| | 0 µM | 1 µM | 10 µM | 100 µM |
| Transformation frequency | 3.2% + 3.46 | 7.6% + 2.19 | 7.5% + 3.23 | 4.5% + 2.86 |

*Data collected from analysis of transgenic plants after rooting

TABLE 13

Soybean transformation media used in this invention

| Component | Infection | Cocultivation | Recovery |
|---|---|---|---|
| MS Basal Salts | 2.15 g/l | 2.15 g/l | — |
| Sucrose | 20 g/l | 20 g/l | 30 g/l |
| Glucose | 10 g/l | 10 g/l | — |
| MES 100 mg/ml | 40 ml | 40 ml | 10 ml |
| B5 Vitamins 200x | 5 ml | 5 ml | 5 ml |
| Zeatin Riboside, trans isomers 1 mg/ml | 2 ml | 2 ml | — |
| Purified Agar | — | 6 g/l | 7.5 g/l |
| Acetosyringone 40 mg/ml | — | 1 ml | — |
| B5 Basal Salt, Gamborg's | — | — | 3.1 g/l |
| MS Iron 200x | — | — | 5 ml |
| Glutamine 25 mg/ml | — | — | 4 ml |
| Asparagine 25 mg/ml | — | — | 4 ml |
| 6-benylaminopurine (BAP) 1 mg/ml | — | — | 2 ml |
| Ticarcillin 100 mg/ml | — | — | 3 ml |
| Glyphosate 100 mM | — | — | — |
| Cefotaxime 250 mg/ml | — | — | — |
| Vancomycin 100 mg/ml | — | — | — |
| IAA 1 mg/ml | — | — | — |
| Gibberellic acid (GA3) 5 mg/ml | — | — | — |

| Component | Regeneration | Elongation |
|---|---|---|
| MS Basal Salts | — | 4.3 g/l |
| Sucrose | 30 g/l | 30 g/l |
| Glucose | — | — |
| MES 100 mg/ml | 10 ml | 10 ml |
| B5 Vitamins 200x | 5 ml | 5 ml |
| Zeatin Riboside, trans isomers 1 mg/ml | — | 0.5 ml |
| Purified Agar | 7.5 g/l | 8 g/l |
| Acetosyringone 40 mg/ml | — | — |
| B5 Basal Salt, Gamborg's | 3.1 g/l | — |
| MS Iron 200x | 5 ml | 5 ml |
| Glutamine 25 mg/ml | — | 2 ml |
| Asparagine 25 mg/ml | — | 2 ml |
| 6-benylaminopurine (BAP) 1 mg/ml | 1 ml | — |
| Ticarcillin 100 mg/ml | 1.5 ml | — |
| Glyphosate 100 mM | 1 ml | 1 ml |
| Cefotaxime 250 mg/ml | 0.3 ml | 0.3 ml |
| Vancomycin 100 mg/ml | 0.5 ml | 0.5 ml |
| IAA 1 mg/ml | — | 0.1 ml |
| Gibberellic acid (GA3) 5 mg/ml | — | 0.2 ml |

Media listed in Table 13 are prepared in 1 Liter batches.
*Regeneration media: All the melatonin test experiments were performed on 100 mM of glyphosate.
**Elongation media: Medium contains glyphosate within range of 50 mM to 100 mM during the tissue culture period.

References

Peri, A., Lotan, O., Abu-Abied, M., and Holland, D. Establishment of an *Agrobacterium*-mediated transformation system for grape (*Vitis vinifera* L.): The role of antioxidants during grape-*Agrobacterium* interactions. *Nature Biotechnol.* 14(5):624-628, 1996;

Enriquez-Obregon, G. A., Vazquez-Padron, R. I., Prieto-Samsonov, D. L., Perez, M., and Selman-Housein, G. Genetic transformation of sugarcane by *Agrobacterium tumefaciens* using antioxidants compounds. *Biotecnol. Aplication.* 14:169-174, 1997;

Enriquez-Obregon, G. A., Vazquez-Padron, R. I., Prieto-Samsonov, D. L., de a Riva, G. A., and Selman-Housein, G.

Herbicide-resistant sugarcane (*Saccharum officinarum* L.) plants by *Agrobacterium*-mediated transformation. *Planta* 206:20-27, 1998;

Enriquez-Obregoón, G., A., Prieto-Samsónov, D., L., Riva, G., A. de la, Pérez, M., Selman-Housein, G., and Vázquez-Padrón, R., I. *Agrobacterium*-mediated japonica rice transformation: a procedure assisted by an antinecrotic treatment. *Plant Cell Tiss. Organ Cult.* 59(3):159-168; 1999;

Frisch D. A., Harris-Haller L. W., Yokubaitis N. T., Thomas, T. L., Hardin S. H., Hall T. C. Complete Sequence of the binary vector Bin 19. *Plant Molecular Biology* 27:405-409, 1995;

Gustavo, A. R., Gonzalez-Cabrera, J., Vazquez-Padron, R., and Ayra-Pardo, C. *Agrobacterium tumefaciens:* a natural tool for plant transformation. *Electronic J. Biotechnol.* 1(3):118-133, 1998;

Das, D., Reddy, M., Upadhyaya, K., and Sopory, S. An efficient leaf-disc culture method for the regeneration via somatic embryogenesis and transformation of grape (*Vitis vinifera* L.). *Plant Cell Rep.* 20(11):999-1005; 2002;

Olhoft, P. M., Lin, K., Galbraith, J., Nielsen, N. C., and Somers, D. A. The role of thiol compounds increasing *Agrobacterium*-mediated transformation of soybean cotyledonary-node cells. *Plant Cell Rep.* 20:731-737, 2001a;

Olhoft, P. M. and Somers, D. A. 1-Cysteine increases *Agrobacterium*-mediated T-DNA delivery into soybean cotyledonary-node cells. *Plant Cell Rep.* 20:706-711, 2001b;

Olhoft, P. M., Flagel, L. E., Donovan, C. M., and Somers, D. A. Efficient soybean transformation using hygromycin B selection in the cotyledonary-node method. *Planta* 216: 723-735, 2003;

Dan, Y., Munyikawa, T. R. I., Kimberly, A. R., and Rommens, C. M. T. Use of lipoic acid in plant culture media. US Patent Pub. No.: US 2004/0133938 A1, 2004;

Dan, Y. A novel plant transformation technology—Lipoic acid. *In Vitro Cell. Dev. Biol. Plant* 42:18-A, 2006 (Abstract);

Dan, Y., Yan H., Munyikwa, T, Dong, J., Zhang, Y., and Armstrong, C. L. MicroTom—A High-Throughput Model Transformation System for Functional Genomics. *Plant Cell Rep.* 25:432-441; 2006;

Dan, Y., (2008) Biological Functions of Antioxidants in Plant Transformation. In Vitro Cell Dev Biol.-Plant 44 (3) 149-161, 2008).

Dekeyser et al., Plant Physiol., 90:217-223, 1989

Della-Cioppa et al., Bio/Technology, 5:579-584, 1987

Southern, Mol. Biol., 98:503-517, 1975

Sambrook et al., Molecular Cloning: A Laboratory Manual, Second Edition, Cold Spring Harbor Laboratory Press, Cold Spring Harbor, N.Y., 1989

Murashige and Skoog, Physiol. Plant, 15:473-497, 1962

Chu et al., Scientia Sinica 18:659, 1975

Linsmaier and Skoog, Physio. Plant., 18: 100, 1965

Uchimiya and Murashige, Plant Physiol. 15:473, 1962

Gamborg et al., Exp. Cell Res., 50:151, 1968

Duncan et al., Planta, 165:322-332, 1985

McCown and Lloyd, HortScience 16:453, 1981

Nitsch and Nitsch, Science 163:85-87, 1969

Schenk and Hildebrandt, Can. J. Bot. 50:199-204, 1972

What is claimed is:

1. A plant transformation media, comprising an effective amount of melatonin or an analog thereof, wherein the said melatonin or analog thereof has a positive effect on plant transformation efficiency.

2. The plant transformation media of claim 1, wherein the amount of melatonin or an analog thereof in the plant transformation media is from about 1 µM to about 2000 µM.

3. The plant transformation media of claim 1, wherein the amount of melatonin or an analog thereof in the plant transformation media is from about 5 µM to about 1500 µM.

4. The plant transformation media of claim 1, wherein the amount of melatonin or an analog thereof in the plant transformation media is from about 10 µM to about 500 µM.

5. The plant transformation media of claim 1, wherein the plant transformation media is suitable for inoculation of plant cell or plant tissue with *Agrobacterium*.

6. The plant transformation media of claim 1, wherein the plant transformation media is suitable for co-cultivation of plant cell or plant tissue with *Agrobacterium*.

7. The plant transformation media of claim 1, wherein the plant transformation media is suitable for the selection of transformed plant cells or tissues.

8. The plant transformation media of claim 1, wherein the plant transformation media is suitable for regeneration of transformed plant cells or tissues into whole fertile plants.

9. The plant transformation media of claim 1, wherein the plant is a monocotyledonous plant.

10. The plant transformation media of claim 1, wherein the plant is a dicotyledonous plant.

11. The plant transformation media of claim 9, wherein the plant is a tomato plant.

12. The plant transformation media of claim 9, wherein the plant is a soybean plant.

13. The plant transformation media of claim 10, wherein the plant is a rice plant.

* * * * *